United States Patent
Sangani et al.

(10) Patent No.: US 6,645,338 B1
(45) Date of Patent: Nov. 11, 2003

(54) STRETCHABLE TAPE

(75) Inventors: Nailesh M. Sangani, Mentor, OH (US); Michael D. Hilston, Painesville, OH (US); Carol A. Caldwell, Lake Bluff, IL (US)

(73) Assignee: Avery Dennison Corporation, Pasadena, CA (US)

( * ) Notice: Subject to any disclaimer, the term of this patent is extended or adjusted under 35 U.S.C. 154(b) by 0 days.

(21) Appl. No.: 10/222,642

(22) Filed: Aug. 16, 2002

Related U.S. Application Data

(62) Division of application No. 09/854,747, filed on May 14, 2001, now Pat. No. 6,463,633.

(51) Int. Cl.⁷ .......... B32B 31/06; B32B 31/18; A61F 13/15; C09J 7/02; A44B 21/00
(52) U.S. Cl. .......... 156/289; 156/247; 156/277; 156/257; 156/259; 156/344; 604/389; 604/390; 24/304; 24/DIG. 11; 428/40.1; 428/41.8; 428/42.2; 428/352
(58) Field of Search .......... 156/230, 247, 156/277, 289, 250, 256, 257, 259, 344; 604/389, 390, 391; 24/304, DIG. 11; 428/40.1, 41.7, 41.8, 42.2, 195, 914, 343, 352, 317.3

(56) References Cited

U.S. PATENT DOCUMENTS

| | | | |
|---|---|---|---|
| 3,159,930 A | 12/1964 | Allen et al. | 40/2 |
| 3,776,234 A | 12/1973 | Hoey | 128/287 |
| 3,800,796 A | 4/1974 | Jacob | 128/284 |
| 3,833,456 A | 9/1974 | Reed et al. | 161/167 |
| 3,874,893 A | 4/1975 | Cherrin | 117/15 |
| 3,893,460 A | 7/1975 | Karami | 128/287 |
| 4,005,713 A | 2/1977 | Meek | 128/287 |
| 4,020,842 A | 5/1977 | Richman et al. | 128/287 |
| 4,051,853 A | 10/1977 | Egan, Jr. | 128/287 |
| 4,066,081 A | 1/1978 | Schaar | 128/287 |
| 4,068,028 A | 1/1978 | Samonides | 428/40 |
| 4,090,516 A | 5/1978 | Schaar | 24/DIG. 11 |
| 4,107,811 A | 8/1978 | Imsande | 15/215 |
| 4,299,223 A | 11/1981 | Cronkrite | 128/287 |
| 4,522,853 A | 6/1985 | Szonn et al. | 428/40.1 |
| 4,643,729 A | 2/1987 | Laplanche | 604/389 |
| 4,671,003 A | 6/1987 | Vitol | 40/2 R |
| 4,726,971 A | 2/1988 | Pape et al. | 428/40 |
| 4,787,158 A | 11/1988 | Vitol | 40/638 |
| 4,787,897 A | 11/1988 | Torimae et al. | 428/343 |
| 4,795,456 A | 1/1989 | Borgers et al. | 604/390 |
| 4,801,480 A | 1/1989 | Panza et al. | 428/40 |
| 5,620,780 A | 4/1997 | Krueger et al. | |
| 5,779,691 A | 7/1998 | Schmitt | 156/183 |
| 6,159,584 A | 12/2000 | Eaton et al. | 428/198 |
| 6,221,483 B1 | 4/2001 | Hilston et al. | 428/343 |
| 6,365,793 B1 * | 4/2002 | McLaughlin et al. | 604/359 |

FOREIGN PATENT DOCUMENTS

| | | |
|---|---|---|
| WO | WO 93/22996 | 11/1993 |
| WO | WO 96/03101 | 2/1996 |

* cited by examiner

Primary Examiner—J. A. Lorengo
(74) Attorney, Agent, or Firm—Pearne & Gordon LLP

(57) ABSTRACT

A stretchable tape includes a nonextensible layer having a separation line, a pressure-sensitive adhesive layer, an extensible layer and an adhesive inhibiting masking between adjacent portions of the extensible layer and adhesive layer to enable relative movement and tape stretchability. The tape is especially useful in the manufacture of diaper tabs. The tape stock and diaper tabs may be manufactured using conventional web processing equipment.

15 Claims, 7 Drawing Sheets

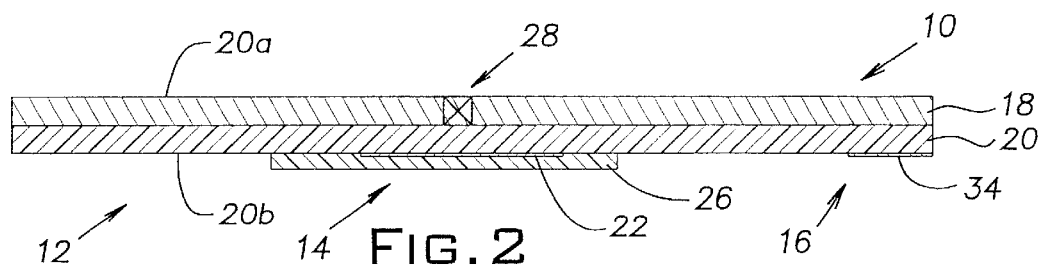
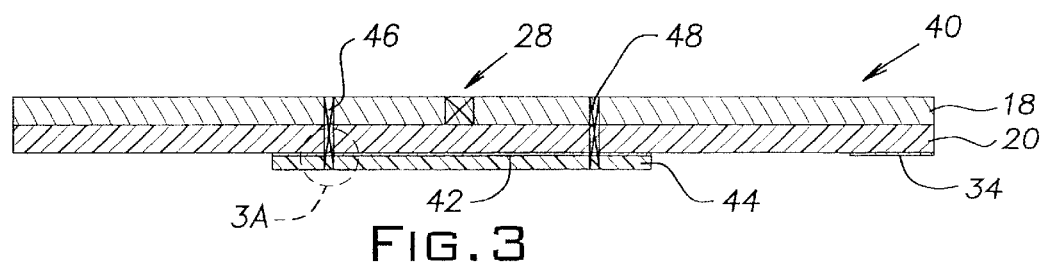
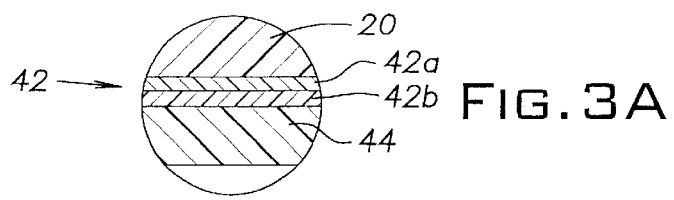
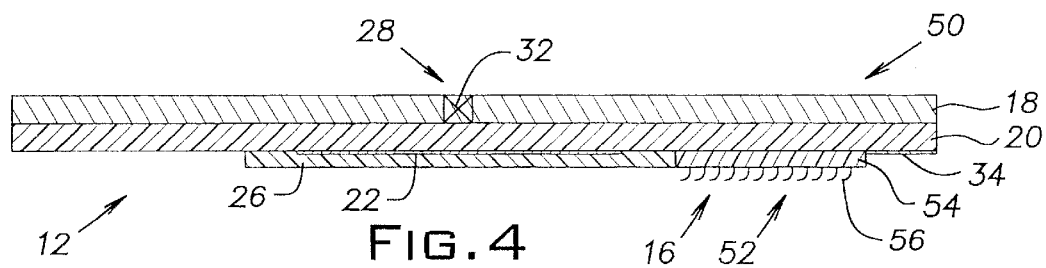
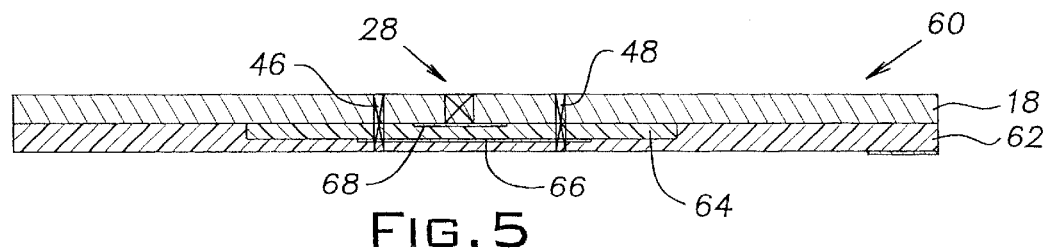

STRETCHABLE TAPE

This application is a division of U.S. application Ser. No. 09/854,747, filed May 14, 2001 now U.S. Pat. No. 6,463,633.

This invention relates to pressure-sensitive adhesive tapes, adhesive tabs formed therefrom, and methods for manufacturing the same. In one aspect, the invention relates to improvements in stretchable tapes and like products, and in the manufacture of the same. In this aspect, the stretchable tapes are formed of multiple layers that are manually stretchable to enable their stretchable properties. In another aspect, the invention relates to improvements in laminate web constructions of diaper fastener-tab stock of the kind adapted to be supplied to a diaper manufacturer and to be separated by the manufacturer into individual diaper-fastening tabs and applied to individual diapers, usually two tabs to a diaper for infant diapers and six tabs to a diaper for adult diapers. In this aspect, the invention particularly relates to means forming part of the diaper tabs and providing novel conveniently manipulated fingerlifts for the tabs.

The tapes are useful in a wide range of applications and constructions wherein a stretchable or variable length connector is required and/or a closing tension is to be applied to two elements as in a protective cover or item of personal clothing such as a gown. The tapes may be used as a construction film for forming an element of a more comprehensive tape or closure system including industrial or craft applications requiring pieces to be secured together with tension during a drying cycle or medical applications such as medical tapes, suture tapes, nasal dilators, bandages and the like. In such broad applications, the tape layers may be formed of polymeric, stretchable polymer and fabric constructions and cellulosic materials. The tapes are especially useful in connection with diaper fastening systems, and they are described hereinafter with particular reference to stretchable fastening tapes for use in diapers, diaper tabs and the manufacture of the foregoing.

RELATED ART

The use of stretchable or extensible fastening tapes in diaper tabs to promote user comfort through better fit and more secure mounting is known in the art. The tabs operate as extensible diaper side waist bands. Examples of such diaper fastening systems are disclosed in U.S. Pat. Nos. 4,795,456, 4,066,081, 4,051,853 and 3,800,796. The teachings of these patents are incorporated herein by reference.

It has been previously proposed to make articles from pressure-sensitive adhesive tapes in which the layer of pressure-sensitive adhesive is partially covered with a printed pattern of ink or other non-printed masking agents such as talc. For example, document or envelope containers are shown in U.S. Pat. Nos. 3,159,930 and 3,874,893, labels are shown in U.S. Pat. No. 4,068,028, a tacky floor mat is taught in U.S. Pat. Nos. 4,107,811 and sign stock is described in U.S. Pat. Nos. 4,671,003 and 4,787,158.

Various fingerlift arrangements specific to diaper tabs are also known in the prior art. One simple arrangement is to provide an adhesive-free zone at the fingerlift edge, as in U.S. Pat. No. 3,833,456 to Reed et al. This fingerlift edge can be difficult to grasp; there is no clear indication of the presence of a fingerlift, and the unsupported edges of rolls from which such tabs are cut can be easily damaged.

Another fingerlift arrangement for a diaper tab is a fold-over arrangement, as in U.S. Pat. No. 3,893,460 to Karami. If such folding-over is done during manufacture of the diaper fastener stock, differences in thickness are created across the width of the stock, causing distortions when the stock is rolled up for storage and shipment. On the other hand, if the folding-over is delayed only to be attempted on the diaper line, the difficulty of performing that step as part of the fastener dispensing and application procedure on the diaper line presents a risk of line stops and delays in diaper production.

Another known fingerlift arrangement for a diaper tab is a strip lamination, as in U.S. Pat. No. 4,726,971 to Pape et al. The laminated strip extends outwardly of the width of the diaper fastener stock, so that when the same is rolled and transported, the laminated strip can be easily damaged. Also, the strip creates local thickness variations in the roll.

Still another arrangement is a pull string, as in U.S. Pat. No. 4,005,713 to Mesek. This too may cause thickness variations, and may be complicated to fabricate and manipulate, particularly at high diaper line speeds.

SUMMARY OF THE INVENTION

The inventive stretchable tape has a multiple layer construction including an adhesive layer for tape mounting of normally nonextensible and extensible layers that selectively bear tension loads. An adhesive-inhibiting masking is applied to a portion of the adhesive layer to enable relative movement between the extensible layer and adjacent adhesive layer portion to thereby provide the tape with stretchable properties.

The stretchable tape includes opposed terminal segments and a central segment. The nonextensible layer typically comprises a facestock material or substrate extending along the length of the tape. The extensible layer and adhesive masking are located adjacent the central segment. A separation line or plane is provided at the central segment.

The separation line may comprise a location of fully separated portions of the facestock or nonextensible layer, such portions being respectively associated with opposed terminal segments, or a weakened joint in the facestock layer that may be ruptured by manual stretching of the tape. The weakened joint may be formed by a tape supplier, a tape converter or an ultimate tape user such as a diaper manufacturer. The weakened joint may be formed in the facestock layer by mechanical or chemical techniques. Mechanical techniques include forming discontinuities along a failure line as by scoring, perforating, slitting or any other means known in the art. Chemical techniques include acid drip or etching.

As it relates to a fastening tape or diaper tab herein, the facestock layer has tear strength or modulus characteristics that enable it to be manufactured and processed in customary web or film sizes using conventional automated machinery that impose insufficient forces to rupture, plastically stretch or otherwise detrimentally deform the layer. The separation lines extend in the machine direction and do not tend to interfere with machine direction forces applied to the stock to carry it through the processing.

For diaper applications, the length of the fastening tape is formed in the machine cross direction and transverse direction of the stock, so that the separation line extends across the width of the tape. If the separation line comprises complete partitioning of the facestock layer, the portions of the facestock layer may simply separate to allow tape stretchability. If the separation line is a weakened joint, the tape may be manually stretched to rupture the facestock layer along the joint, and thereby transfer stretching forces to the extensible layer and achieve stretchable tape or tab properties.

In another aspect, the adhesive masking may provide a distinctive color appearance as by phosphorescence or fluorescence. This distinctive color appearance may be provided for any number of applications including designation of location of control or manipulative elements.

In diaper applications, the high visibility of the fingerlift provided by the phosphorescence or fluorescence is useful in typical household infant diaper applications. It is especially useful in a health care facility when it is not desirable to fully light the room and disturb the patient whose diaper is to be checked or changed. Further, the distinctive appearance may serve as a warning to avoid contact. For example, the protective latex gloves worn by the attendant or nurse may be torn if the pressure-sensitive adhesive is inadvertently contacted and then pulled-free.

In contrast with the prior art use of adhesive barriers, in the present invention as it relates to tapes, the adhesive masking is provided along a continuous zone or line using web processing apparatus and techniques. In addition to enabling relative movement between adjacent layers as noted above, the continuous application of the adhesive masking may form end fingerlifts.

In one aspect, the present invention involves the concept of utilizing such means to eliminate or minimize complications, constraints and disadvantages involved in pattern-coating substrates with pressure-sensitive adhesive in the manufacture of tapes and other articles. In particular, the invention minimizes or eliminates complications, constraints and disadvantages involved in the need to pattern-coat the adhesive.

The adhesive masking is applied along continuous stripes or zones in a selected masking pattern corresponding with required areas of adhesive deadening to eliminate the need for pattern coating of the adhesive. The-masking may be applied in a high speed web processing technique such as printing, roll-coating, extrusion or coextrusion.

The adhesive masking also enables the adhesive layer to be continuous at the separation line so that adjacent portions of the web material tend to remain in the plane of the web during processing. In contrast, pattern coated webs do not have adhesive adjacent the separation line. More particularly, "gaps" exist between spaced portions of the pattern coated adhesive as shown in U.S. Pat. No. 4,795,456, which patent is also owned by the assignee of this application. The overlying portions of the facestock layers at such gaps may tend to move out of the plane of the web or fold-over during processing so as to expose interior layers which may have a different coefficient of friction as compared with the surface of the web normally intended to be exposed.

Upon exposure of such an interior layer, it may interfere with uniform travel of the layers along roller surfaces or other friction supporting members due to its different coefficient of friction. This is particularly troublesome upon exposure of an interior extensible layer which tends to have a significantly higher coefficient of friction. In order to more closely match the coefficients of these surfaces, it is known in the art to emboss the surface of the extensible layer in order to reduce its coefficient of friction. The present invention eliminates the need for such an embossing step.

The invention enables the manufacture of fastening tape stock and diaper fastener or tab stock of substantially uniform thickness from one edge to the other, with attendant advantages to the manufacturer and converter. Also, a stripe of the masking agent may be applied to the outer most edges of the stock in order to provide adhesive-free and therefore "pick"-free roll edges.

The invention also enables stretchable tape to be formed with continuous line production techniques including applying adhesive inhibiting masking along selected continuous stripes of the adhesive surface using high-speed line processes such as printing, roll coating, extrusion and coextrusion. The adhesive masking may be a single layer construction or a multiple layer construction to provide function specific layers to enhance adhesion, cohesion, bonding or friction properties.

In accordance with the foregoing improvements, the invention provides for the manufacture of stretchable diaper fastener or tab stock, and stretchable diaper fastening tabs formed from such stock, in a manner compatible with current diaper manufacturing practice, providing improved diaper tabs, and improved tabbed diapers, at little or no increase in costs over the practices of the prior art.

In this respect, the present invention also provides diaper tab fasteners having fingerlifts (i.e., end tabs for the tab fasteners themselves) which are "built-in," which are easy and convenient to use, which overcome the problems of the prior art diaper tab fingerlifts including thickness variations and added material costs, and which offer new advantages including the ability to economically provide improved distinguishability of the fingerlifts from the remainder of the tabs, the ability to provide for the absorption of finger oils or other contaminants, and the ability to add fragrances to the tabs. The distinguishability may be further enhanced by use of adhesive masking having phosphorescence or fluorescence properties.

In a further aspect, the present convention relates to transfer tapes wherein the pressure sensitive adhesive layer is partially covered with a selected pattern of the adhesive masking. Once again, the adhesive masking is applied along continuous zones or stripes. The tape is formed in a whole or in part by slitting along the continuous stripe through the tape substrate, the adhesive coating and the adhesive masking. In this manner, the need to pattern coat the substrate with pressure sensitive adhesive in the manufacture of transfer tapes and other articles is eliminated.

Accordingly, the present invention overcomes the inability to slit rolls of pre-manufactured transfer tape stock to various widths on demand, and eliminates the corresponding need to manufacture and inventory various widths of transfer tape pending demand for one or the other specific width or widths. The invention enables the manufacture of tape stock and tapes with attendant advantages to the manufacturer and converter. The transfer tapes may be used in the manufacturer of the stretchable tapes, fastening tapes, tape stocks, diaper tabs and diaper tab stock in accordance with the invention.

BRIEF DESCRIPTION OF THE DRAWINGS

The features and advantages of the invention will be more fully understood from the following description of specific examples, together with the drawings, in which:

FIG. 2 is a cross-sectional view taken along the line 2—2 in FIG. 1;

FIG. 3 is a cross-sectional view similar to FIG. 2 of another embodiment of a stretchable tape in accordance with the invention;

FIG. 3A is a cross-sectional view on an enlarged scale of the details of the indicated portion of FIG. 3;

FIG. 4 is a cross-sectional view similar to FIG. 3 of another embodiment of a stretchable tape having a mechanical fastener in accordance with the invention;

FIG. 5 is a cross-sectional view similar to FIG. 3 of another embodiment of the invention;

DETAILED DESCRIPTION OF THE DRAWINGS

Figure 1:
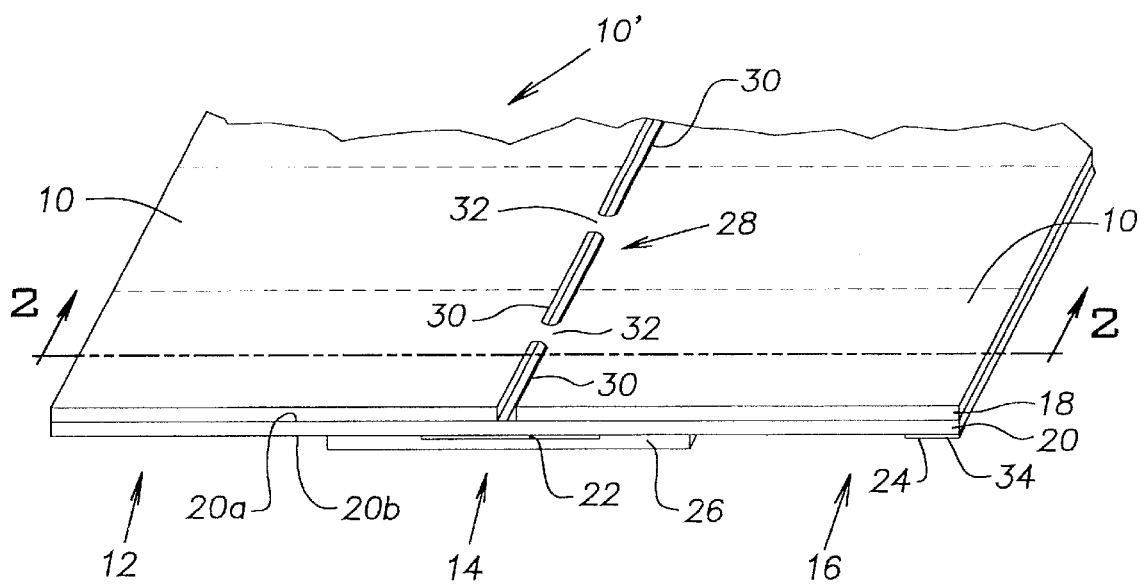
FIG. 1 is a sectional isometric showing a stretchable tape stock in accordance with the invention, with certain details and dimensions exaggerated for clarity of illustration.

Referring to FIGS. 1 and 2, a stretchable diaper fastening tape 10 is shown prior to being transversely cut from single-wide tape stock 10'. More particularly, two identical fastening tapes 10 may be cut along the dotted lines shown in FIG. 1. For convenience, a single tape 10 is described hereinafter.

The tape 10 includes a first terminal segment or outer end portion 12, a central segment 14 and a second terminal segment or outer end portion 16 in its lengthwise direction. In its thickness direction, the tape 10 includes a nonextensible facestock layer 18, an adhesive layer 20, adhesive-inhibiting masking layers 22 and 24, and an extensible layer 26.

A separation line or plane 28 is located within the central segment 14. The separation line 28 is formed by slits 30 and connecting ties 32. In FIG. 1, a full slit and portions of two neighboring slits 30 are shown together with two intermediate ties 32. The slits 30 extend in a width direction in respect to the tape 10 and through the thickness of the layer 18 and, as indicated above, the slits 30 are intermittently interrupted by maintenance of the layer 18 to form the tie 32. It is not necessary for the slit 30 to extend through the adhesive layer 20 since the latter has essentially no mechanical strength. Preferably, at least one tie 32 is provided in the separation line 28 extending along the width of the tape 10.

The adhesive layer 20 includes a surface 20a secured to the surface of the layer 18 and a remote surface 20b. The portion of the surface 20b adjacent the first terminal segment 12 may be used to mount the fastening tape 10 to a release tape as part of a factory joint in a diaper application or to any other mounting surface. The portion of the surface 20b adjacent the second terminal segment 16 may be used to close a diaper about an infant or wearer by securing it to a front diaper panel (not shown) in a known manner in a user joint.

The adhesive inhibiting masking layer 22 is provided along the surface 20b of the adhesive layer 20 within the central segment 14 of the tape 10 adjacent the separation line 28. The masking layer 22 extends across the entire width of the tape 10 and along at least a portion of the length of the tape within the central segment 14 of the tape 10. Portions of the adhesive layer 20 on each side of the masking layer 22 respectively secure the elastic layer 26 to the layer 18 adjacent the first and second terminal segments 12 and 16 of the tape 10.

The masking layer 22 effectively deadens or inhibits the adhesive properties of the adhesive layer 20 to allow relative movement between the elastic layer 26 and the adhesive layer 20. Upon manually stretching the tape 10, the tie 32 fails or ruptures and the further tensile loads applied to the tape 10 are transferred to the elastic layer 26 to provide stretchable characteristics to the tape 10. That is, following rupture of the tie 32, the tape 10 may be stretched within the elastic limit of the layer 26 and allowed to recover.

The masking layer 24 provides a fingerlift 34 adjacent the terminal segment 16 of the tape 10. As shown, the fingerlift 34 is provided at the remote extremity of the segment 16.

Referring to FIG. 3, a diaper fastening tape 40 a shown. For convenience, elements of the tape 40 corresponding with those of the tape 10 are identically numbered. Accordingly, the tape 40 includes a facestock layer 18 and a pressure sensitive adhesive layer 20. An adhesive inhibiting masking layer 42 extends along substantially the entire length of an elastic layer 44. The elastic layer 44 is secured to the adhesive and the layer 18 by thermal bonding such as ultrasonic bonds 46 and 48. The masking layer 42 provides relative movement between the adhesive layer 20 and the elastic layer 44 between the ultrasonic bonds 46 and 48. The distance between the ultrasonic bonds 46, 48 may be selected to provide the desired range of relative movement and corresponding stretchable properties of the tape 40.

Referring to FIG. 3A, the masking layer 42 includes multiple layers 42a and 42b. These layers may be provided by overlying printing, coating or extrusion passes as well as by coextrusion processing.

The layers 42a and 42b may be function specific and/or cost selected. For example, the layer 42a may provide good ultrasonic bonding properties and the layer 42b may provide good adhesion deadening properties and/or cohesive properties with respect to the extensible layer 44 as described in U.S. Pat. No. 5,085,655. Of course, one or more of the layers may be formed of a cost effective relatively inexpensive composition.

Referring to FIG. 4, a fastening tape 50 is shown. The tape 50 is similar to the tape 10 and, once again, corresponding elements are similarly numbered. The tape 50 includes a facestock layer 18 and a pressure sensitive adhesive layer 20, and an adhesive inhibiting masking layer 22 extending along a portion of an elastic layer 26. The elastic layer 26 is secured to the adhesive layer 20 and the layer 18 adjacent the lengthwise extremities of the layer 22. As in the above embodiment of FIG. 1, the layer 22 provides relative movement between the adhesive layer 20 and the elastic layer 26.

The tape 50 includes a first terminal segment or inner end portion 12 along which the adhesive layer 20 forms a factory joint with a diaper (not shown). Adjacent the second terminal segment or outer end portion 16 of the tape 50, a mechanical faster 52 is provided for securing the tape in a user joint. The fastener 52 may cover all or part of the portion of the adhesive 20 between the layer 26 and the fingerlift 34.

The fastener 52 includes a substrate 54 secured to the adjacent portion of the adhesive layer 20 and carrying engaging elements 56. The elements 56 may be provided as the hook portion of a hook and loop closure system, the loop portion (not shown) may be carried by a reinforcing front panel of a diaper (not shown).

Referring to FIG. 5, a fastening tape 60 includes a facestock layer 18, a pressure sensitive adhesive layer 62 and an intermediate extensible layer 64. Relative movement between the layer 62 and 64 is provided by an adhesive inhibiting masking layer 66. The multiple layer assembly is secured together by ultrasonic bonds 46 and 48. The distance between the ultrasonic bonds 46 and 48 determines the extent of the relative movement between the adhesive layer 62 and elastic layer 64 and the stretchability of the tape.

In addition, a masking layer 68 is provided on the surface of the elastic layer 64 adjacent the separation line 28. If the separation line 28 opens during machine processing of tape stock 10', the coefficient of friction of the layer 68 is closer to that of the layer 18 than that of the layer 64. The matching of coefficients is desirable to maintain uniform and straight tracking of the tape stock 10' through the processing machinery.

Figure 6:
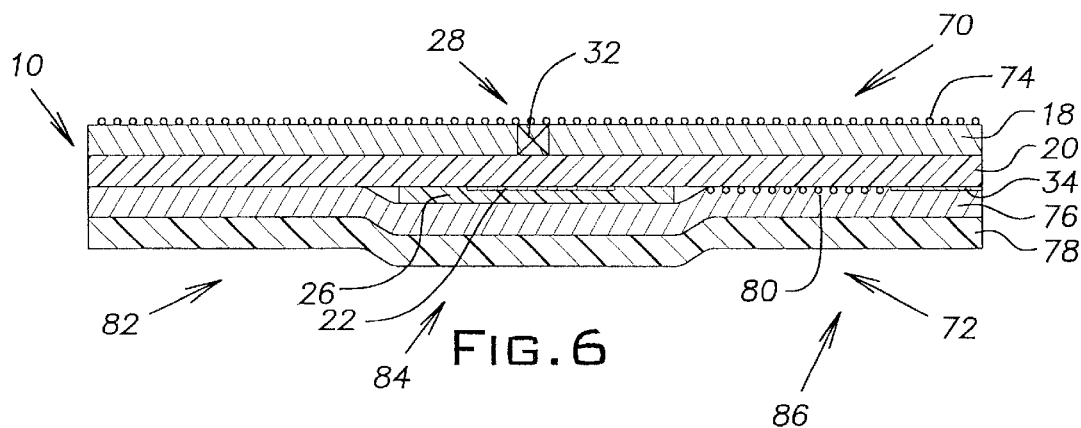
FIG. 6 is a cross-sectional view of a stretchable diaper tab including a fastening tape and a release tape in accordance with the invention.

Referring to FIG. 6, a stretchable diaper tab or fastener 70 includes as its principal components the fastening tape 10 and a release tape 72. The individual fastener 70 as shown in FIG. 6, corresponds with a cross-sectional view of the fastener stock from which the individual fastener may be formed by transverse cuts. For purposes of self-winding the stock material, a release coat 74 of known silicone or carbamate compositions is applied to the exposed surface of the fastening tape 10.

The release tape 72 includes a substrate or facestock layer 76 having a coating of pressure sensitive adhesive 78. A release coat 80 extends along a lengthwise portion of the surface of the substrate layer 76 adjacent to the adhesive layer 20 of the tape 10. The release coat 80 will have a harder release than that of the release coat 74.

The release tape 72 includes a first terminal segment or outer portion 82, a central segment or portion 84 and a second terminal segment or outer portion 86. As shown, extensible layer 26 together with adhesive masking 22 are positioned within the central segment 84. Similarly, separation line 28 is located at the central segment 84.

The facestock layers 18 and 76 may be formed of film-forming thermoplastic polymers having the same or different compositions. The thermoplastic polymer may be a polyolefin such as polyethylene, polypropylene, poly(ethylene-propylene), poly(ethylene-vinyl acetate), poly(styrene-butadiene), or copolymers or blends thereof. A minor amount of an ethylene-propylene component may be incorporated in the thermoplastic polymer. Polypropylene is a preferred thermoplastic polymer. Films of such polymers, e.g. 0.1 to 20 mils thick, exhibit little or no recovery from stretching or deformation and exemplify the nonextensible or inelastic properties of interest herein.

Each of the extensible layers 26, 44 and 64 may be formed of one or more polymers, copolymers or blends or mixtures thereof. The polymeric materials may be applied in any convenient technique including lamination, coating, transfer coating, extrusion and coextrusion. It is also possible to form the extensible layer of an elastic band material incorporated into the fastening tape using a lamination technique.

The extensible layer may range in thickness from about 0.1 to about 40 mils. The thickness may vary in accordance with modulus of the material or materials forming the extensible layer. In diaper applications, the thickness may range from about 2 to about 30 mils and, more preferably, from about 4 to about 8 mils.

Preferred compositions for forming the extensible layers 26, 44 and 64 include thermoplastic elastomers as taught in U.S. patent application Ser. No. 09/151,248, filed Sep. 10, 1998, of common assignee, such patent teachings being incorporated herein by reference. The thermoplastic elastomers of interest are block copolymers having or containing the tetrablock structure A-B-A-D, the triblock structure A-B-A and, optionally, the diblock structure A-B in lesser amounts as a minor component. In such block structures, A represents a block which is non-rubbery or glassy or crystalline at service temperature, e.g. about 100° F. in the case of diaper tapes, and B and D, which may be the same, each represent a block which is rubbery or elastomeric at service temperature. At elevated temperatures, the A, B and D blocks are sufficiently fluid to enable coextrusion of the thermoplastic elastomer. Films of such polymers, e.g. 0.1 to 40 mils thick, exhibit recovery from stretching or deformation below their yield point and exemplify the extensible or elastic properties of interest herein.

The thermoplastic elastomer may be blended with a thermoplastic polymer end block reinforcing agent of relatively high molecular weight, e.g. a molecular weight greater than 2000 and, more preferably, in the range of 3000 to 5000, and higher. Such reinforcing agents improve elevated temperature shear strength.

Preferred reinforcing agents are high molecular weight aromatic compounds such as polyphenylene oxide (or polyphenyl ether) which have molecular weights in the range of 3,000 to 30,000 and higher. These reinforcing agents are added in amounts ranging from 3 to 9, and more preferably, from 8 to 9 parts by weight based on the weight of the elastomer component. Other preferred reinforcing agents comprise pure monomer resins of polycyclic arenes including substituted and unsubstituted vinylarenes such as styrene and methylstyrene. These are used in amounts ranging from 5 to 25, and more preferably, from 12 to 14 parts by weight based on the weight of the elastomer component.

Other conventional additives such as antioxidants, colorants and processing aids may be added.

The pressure sensitive adhesives used in the present convention are well-known in the industry. The adhesives include acrylics, rubber-based hot melts and solvent-based hot melts. For example, the adhesive may be a thermally cross-linked acrylic adhesive, the cross-linking mechanism comprising a metal chelate such as aluminum acetylacetonate (in a small weight percentage, say 0.15%). A suitable adhesive composition for the adhesive layers 20, 62 and 78 has the following formulation:

| | |
|---|---|
| 31.7% | KRATON 1107 (Shell Chemical, polystyrene-isoprene-polystryene linear block copolymer) |
| 46.3% | ESCOREZ 131OLC (Exxon Chemical, solid $C_5$ tackifying resin) 46.3% |

-continued

| | |
|---|---|
| 19.8% | WINGTACK 10 (Goodyear Chemical, solid $C_5$ resin) |
| 1.0% | ETHANOX 330 (Ethyl Corporation, phenolic anti-oxidant) |
| 1.2% | PLASTONOX LTDP (American Cyanimid, thioester anti-oxidant) |

A suitable masking for such adhesive may be formed by printing, using as the ink "Flexo Write on White" CLA 40457F supplied by Sun Chemical Corp. The ink may be thinned with a press solvent to a running viscosity of 20–22 seconds as measured using a No. 2 Zahn Cup. The solvent may be a mixture of 75% normal propyl alcohol, 25% ethyl acetate and 5% "Ektosolve" (Chemcentral). A suitable masking or barrier may be formed by printing, using as the ink "SUNTEX 182 PINK" CLA 40457F supplied by Sun Chemical Corp. The ink may be thinned with the same press solvent and to the same running viscosity as noted above. Other suitable inks or coatable or extruded compositions include DFX 300 Blue, sold by Desco Chem. Inc., a UV curable coating and RC-711, sold by Goldschmidt Chemical, an acrylate silicone, electron beam curable coating.

The thickness of the masking layer is insignificant in that it does not exceed about 3% of the combined thickness of the nonextensible layer or facestock, adhesive layer and extensible layer. The weight of the masking layer is less than about 8 grams per square meter ("gsm"). For example, a printed ink masking layer may have a thickness of about 4 microns.

The separation or release force of the coating 74 is less than that of the coating 80. Illustrative silicone compositions are set forth below.

The following has been used for the lower or easier release coating 74, in weight percentages:

| | |
|---|---|
| 96.10% | Dow SYLOFF 7044 (100% solid, rhodium precatalyzed organofunctional siloxane easy release polymer) |
| 3.90% | Dow Q2-7048 (100% solid reactive polymethylhydrogen siloxane, crosslinker polymer). |

The coating may be applied at 1.5 gsm.

The following has been used for the higher or harder release coating 80:

| | |
|---|---|
| 51.00% | Dow SYLOFF 7044 (100% solid, rhodium precatalyzed organofunctional siloxane easy release polymer) |
| 44.50% | Dow Q2-7069 (100% solid, rhodium precatalyzed organofunctional siloxane easy release polymer) |
| 4.50% | Dow Q2-7048 (100% solid reactive polymethylhydrogen siloxane, crosslinker polymer). |

This coating may be applied at 1.4 gsm.

The release coat 74 allows the construction as so far described to be self-wound for storage and shipment. When the stock of diaper fastener 70 is wound on itself, the release tape adhesive 78 is releasably supported against the release coat 74, and readily separates therefrom when the roll is subsequently unwound on a diaper manufacturing line.

When the roll stock of the diaper fastener 70 is wound as just described, the built-in end tab afforded by the masking layer 24 and associated overlying portion of the layer 18 allows the roll to form evenly without build-up of one side, and presents evenly thick edges which are supported from one turn to the next in the wound roll. On the manufacturing line, the diaper fastener stock is unwound and cut transversely to form a series of individual fasteners which are applied, usually in pairs, to individual diapers by being folded around a diaper edge.

Figure 7:
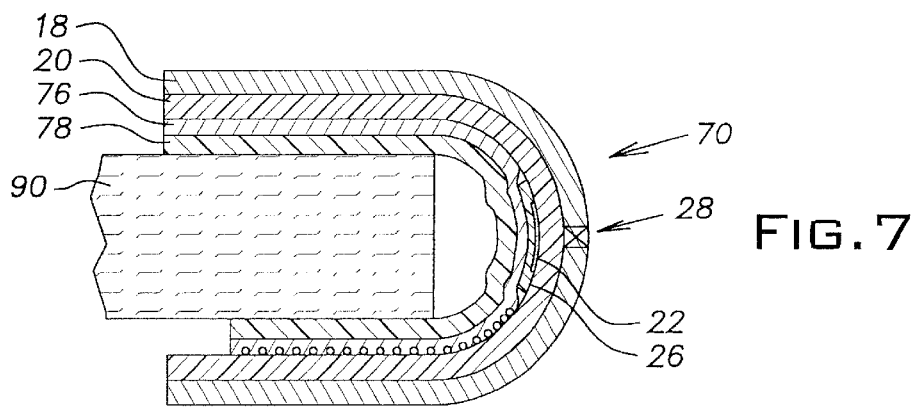
FIG. 7 is a cross-sectional view of an individual diaper tab corresponding to the construction of FIG. 6 applied around the edge of a diaper.

FIG. 7 shows an individual diaper fastener 70 cut from the stock described above applied around the edge of a diaper 90. This is the undeployed or stored condition of the diaper fastener 70. Fasteners made according to the invention have been found to perform satisfactorily when applied to Huggies Super Trim diapers (Kimberly Clark) which, as is typical of many contemporary disposable diaper constructions, have a fastener-receiving frontal tape to reinforce the relatively fragile and easily torn diaper outer plastic shell or envelope.

Figure 8:
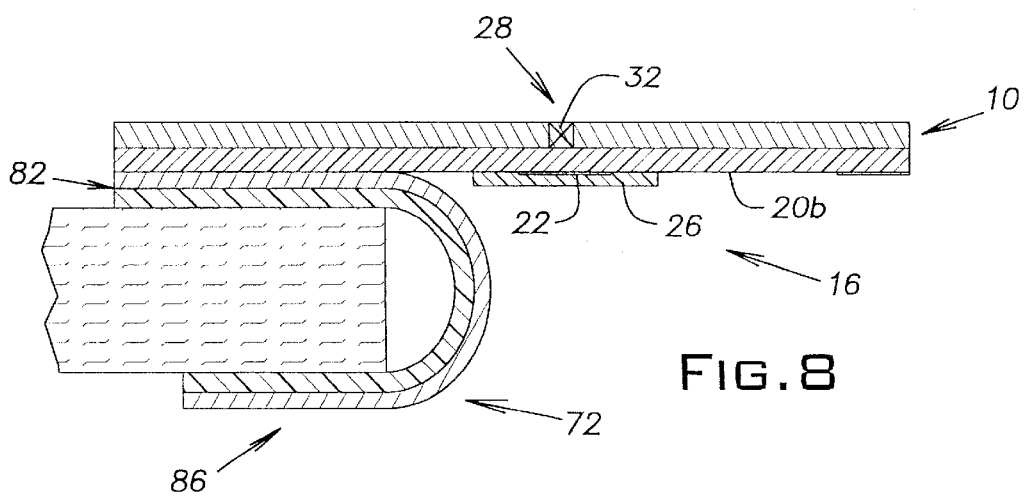
FIG. 8 shows the diaper tab of FIG. 7 deployed for fastening to another part of the diaper.

FIG. 8 illustrates the deployed condition of the diaper fastener 70. When a diaper is applied to an infant or other person, each diaper fastener is moved from undeployed to deployed condition. The second terminal segment or length portion 16 of the fastening tape 10 constitutes deployment means separable from the second terminal segment or length portion 86 of the release tape 72 for deployment as shown in FIG. 8 and adherence to another portion of the diaper (not shown) by application of the exposed second length adhesive 20 to such other diaper portion. The fingerlift 34 is at the free end of the tape 10.

Upon deployment, manual tension loads are initially carried by the facestock layer 18 of the fastening tape 10. However, when such loads exceed the tear strength of the separation line 28, and more particularly, upon rupture of the tie 32 (FIG. 1), the nonextensible layer 18 freely separates or parts along the separation line 28. Thereafter, the tension loads applied to the fastener 70 are carried by the extensible layer 26, and the fastening tape 10 and fastener 70 assume their stretchable properties. The stretchability characteristics are related to the elasticity of the layer 26 and the lengthwise extent or distance along which the masking layer 22 inhibits adhesion between the adhesive layer 20 and the extensible layer 26.

In other words, the fastening tape 10 will be seen to include inner and outer end portions, and which is fastened at its inner end to one part of the diaper 90 via the adhesive layers 20 and 78 and the facestock layer 76 of the release tape 72 (FIG. 7). The tape will be seen to have a pressure-sensitive adhesive face 20b (FIG. 8) at least at the outer end portion thereof, such face being carried on release coat 80 which in turn is carried on the same part of the diaper via the facestock layer 76 and adhesive 78 (FIG. 7). The fastening tape 10 is adapted to have its outer end peeled from and thereby deployed from the part of the diaper seen in FIGS. 7 and 8 for fastening to another part of the diaper (not shown) to thereby establish a user joint and fasten the diaper. The outer end of the fastening tape 10 includes lift tab 34 in the form of the masking layer 24 for initiating peeling of the outer end from the release coat 80.

The masking layers or portions may, if desired, be provided with fragrances, which may simply be added to a printing ink. Absorbent powders in the ink may function to pick off finger oils of the parent or other care giver who handles the diaper tab, thereby reducing the likelihood of contamination of the bonding interface established when the tab is fastened. The ingredients of the masking may have a double function, for example an absorbent powder may contribute both to deactivating or masking the pressure-sensitive adhesive and to. absorbing finger oils.

The color contrast and distinctiveness of the masking agent, and particularly the masking layer 24, may be enhanced by the addition of phosphorescent or fluorescent additives to the above described printing ink. Illustrative phosphorescent and fluorescent additives are described below.

A suitable phosphorescent additive is 6SSU or Lumi Nova sold by United Mineral & Chemical Corp. This additive may be added to the printing ink using conventional blending techniques and in various weight percentages depending upon the desired level of phosphorescence. For example, pigment loadings of 2 to 20% by weight have been found suitable based on desired phosphorescence (glow-in-the-dark).

A suitable fluorescent additive is UVitex OB, commercially available from Ciba Geigy. The fluorescent additive may be combined with the ink as described above. Useful weight percentages range from 50 ppm to 220 ppm.

Additional forms of diaper fasteners utilizing the invention may be provided. Thus, a type of two-substrate tab may be provided wherein both substrates perform an anchoring function, and less substrate material is used than in the designs previously described.

Such diaper stock may be first combined on the diaper manufacturing line from stock components made by different manufacturers. For example, the two substrates and associated adhesives and release coats may be provided in self-wound form from different sources or from a single source.

Figure 9:
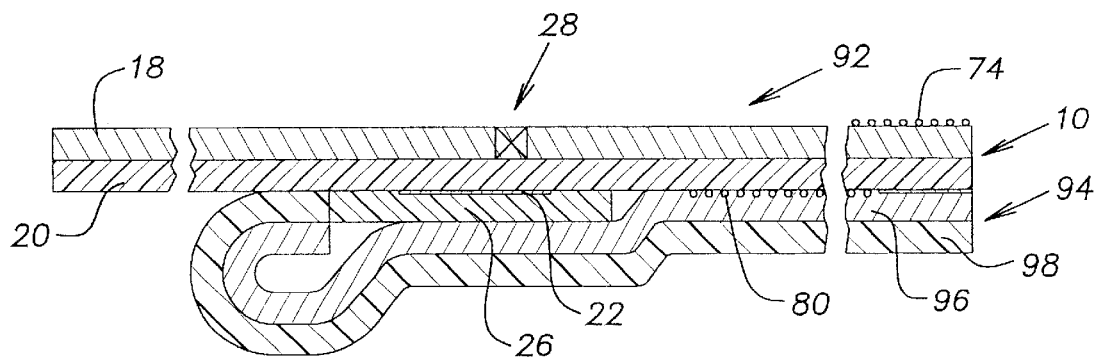
FIG. 9 is a cross-sectional view similar to FIG. 6 of a stretchable diaper tab including a fastening tape and a release tape in accordance with another embodiment of the invention.
Figure 10:
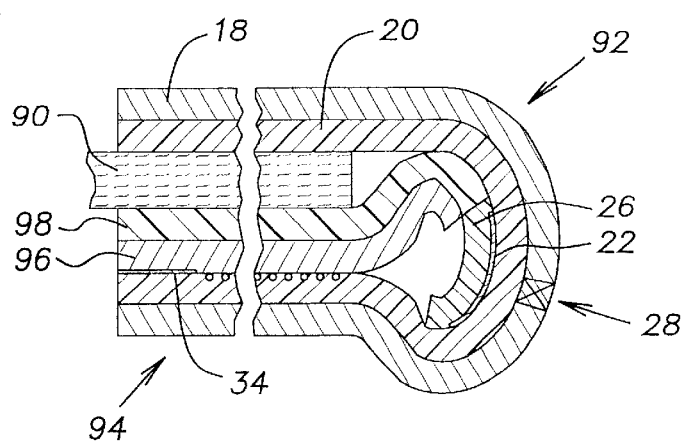
FIG. 10 is a cross-sectional view of a diaper tab corresponding to the construction of FIG. 9 applied around the edge of a diaper.
Figure 11:
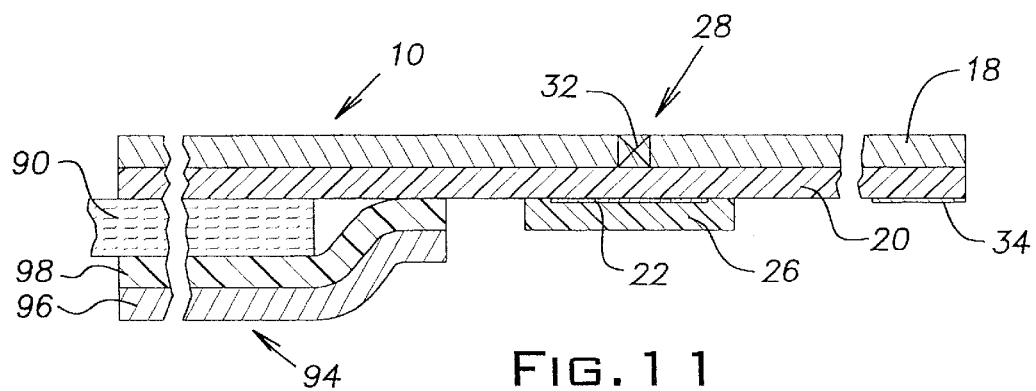
FIG. 11 shows the diaper tab of FIG. 9 deployed for fastening to another part of the diaper.

As shown in FIGS. 9, 10 and 11, a diaper fastener 92 includes fastening tape 10 and a release tape 94. The release tape 94 has a length equal to about one-half of that of the fastening tape 10.

The release tape 94 includes a facestock or substrate layer 96 and a pressure sensitive adhesive layer 98. The compositions of the layers 96 and 98 may be similar to those of the layers 76 and 78 in the embodiment of FIG. 6. Further, release coats 74 and 80 may be similarly employed.

As best shown in FIG. 9, the fastener tape 92 is secured to the diaper 90 in the stored position by the adhesive layer 20 to the outer shell of the diaper and by the adhesive layer 98 to the inside surface of the diaper.

Upon deployment, the outer end portion of the fastening tape 10 is peeled from the substrate layer 96 with the fingerlift 34 assisting to initiate peeling from the release coat 80. Upon manual stretching, any ties 32 that are present along the separation line 28 rupture and the fastening tape 10 assumes its stretchable characteristics. More particularly, tension loads are transferred from the facestock layer 18 to the extensible layer 26 and relative movement between the layers 26 and 20 is allowed by the adhesive masking layer 22.

Figure 12:
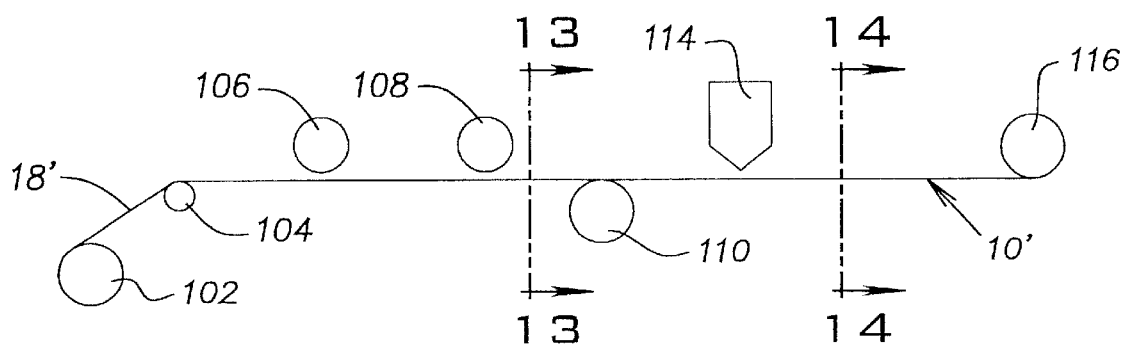
FIG. 12 is a schematic view of a production line for manufacture of a fastening tape as shown in FIG. 1.

Referring to FIG. 12, a manufacturing line 100 for producing roll stock that may be converted to form the tape 10 is schematically shown. For convenience, the precursors of the various elements forming tape 10 are identified with the addition of a prime designation.

Accordingly, a supply roll 102 of facestock stock material 18' is supplied over a guide roll 104. Pressure sensitive adhesive 20' is applied to the surface of the passing stock material 18' at adhesive coating station 106. The adhesive is applied across the full width of the stock material and, upon conversion, forms the adhesive layer 20 of the tape 10.

Figure 13:
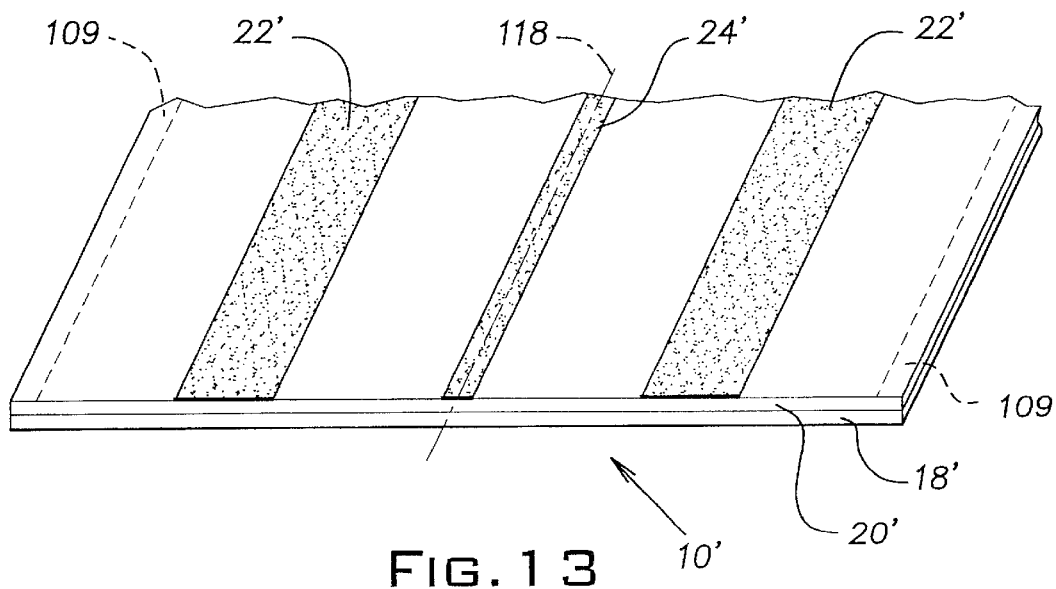
FIG. 13 is a cross-sectional view on an enlarged scale taken along the line 13—13 in FIG. 12.

At printing station 108, stripes of masking layer of 22' and 24' are applied to the surface of the pressure sensitive adhesive 20' as best shown in FIG. 13. optionally, stripes of edge masking 109 (shown in dotted outline) may be formed adjacent the outside edges of the adhesive layer 20' in order to provide adhesive-free and therefore pick-free roll edges.

Figure 15:
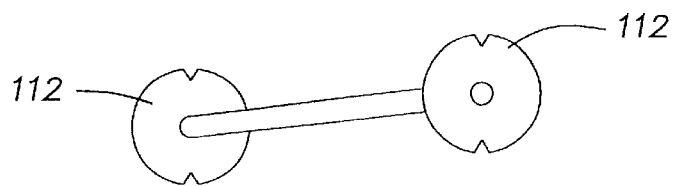
FIG. 15 is a diagrammatic view of a pair of cutter rolls arranged to form separation lines in accordance with the invention.

Following the printing station 108, the tape 10' passes through slitter station 110. Slitter station 110 may include a plurality of notched cutting disks 112 (FIG. 15) positioned along the width of the stock layer to cut separation lines 28'. The disks 112 cut through the thickness of the facestock 18'. It is not necessary to cut the thickness of the adhesive 20' since it has no significant tear strength. That is, upon manual stretching of the tape 10, the adhesive layer 20 will fail along the separation line 28. The slitting step may provide a continuous slit in the machine direction to form a fully separated or cleaved layer 18' and subsequent separation line 28. In such full slit cases, the continuous adhesive layer in the machine cross-direction tends to inhibit the adjacent portions of the slit stock from moving out of the plane of the stock as by folding due to the added adhesive weight. This promotes uniform tracking of the stock or web material through the machine processing.

It should be appreciated that the slitting step may be omitted and subsequently done by a converter or a diaper manufacturer.

Figure 14:
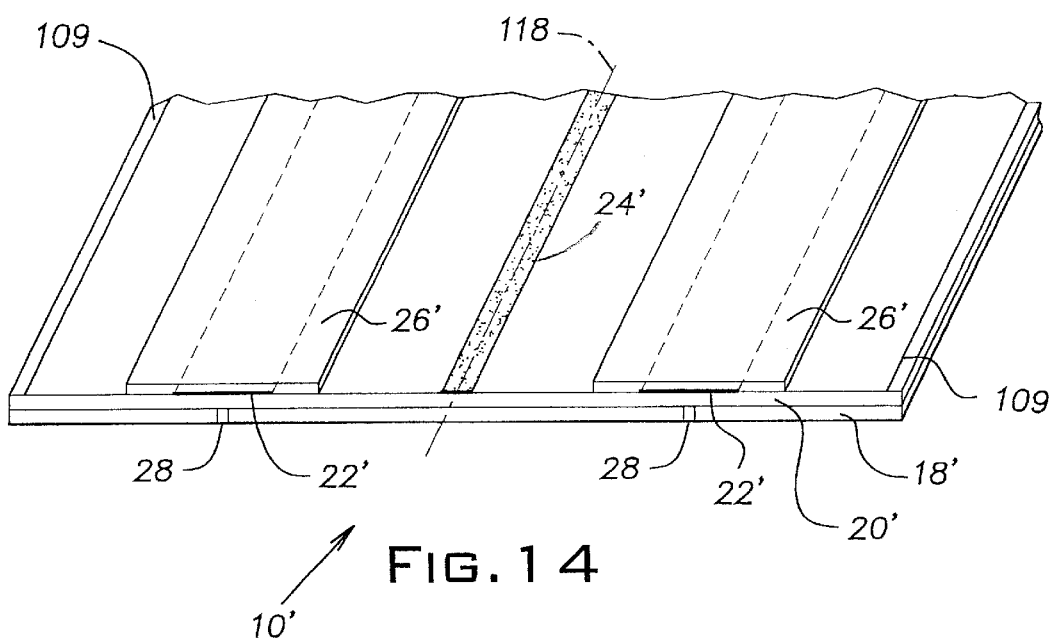
FIG. 14 is a cross-sectional view on an enlarged scale taken along the line 14—14 in FIG. 12.

Referring once again to FIG. 12, the facestock 18' passes from the slitter station 110 to extruder station 114 for application of stripes of extensible or elastic material 26'. As shown in FIG. 14, the stripes of elastic material 26' overly the stripes of masking agent 22'.

The tape stock 10' is wound into a roll 116. The tape stock 10' may be supplied to converters in single or multiple width sizes. Tape stock 10' is sized to provide two lengths of tape 10 when transversely cut along line 118. The tape manufacturer may provide the roll of tape 10' in double widths for cutting by the user or it may be manufactured in single width size.

It should be appreciated that a release tape may be joined to the fastening tape 10' at any convenient location in the processing line. For example, the release tape may be joined to the tape 10' following slitting of the latter at station 110 and prior to rolling. Of course, the release tape may be subsequently combined with the fastening tape 10' by a converter or diaper manufacturer.

If the tape 10' is to be provided with a mechanical fastener 52 as in FIG. 4, the fastener 52' may be joined or laminated to the adhesive layer 20' to the tape 10' at a suitable step in the processing, for example, following the slitting step.

Figure 16:
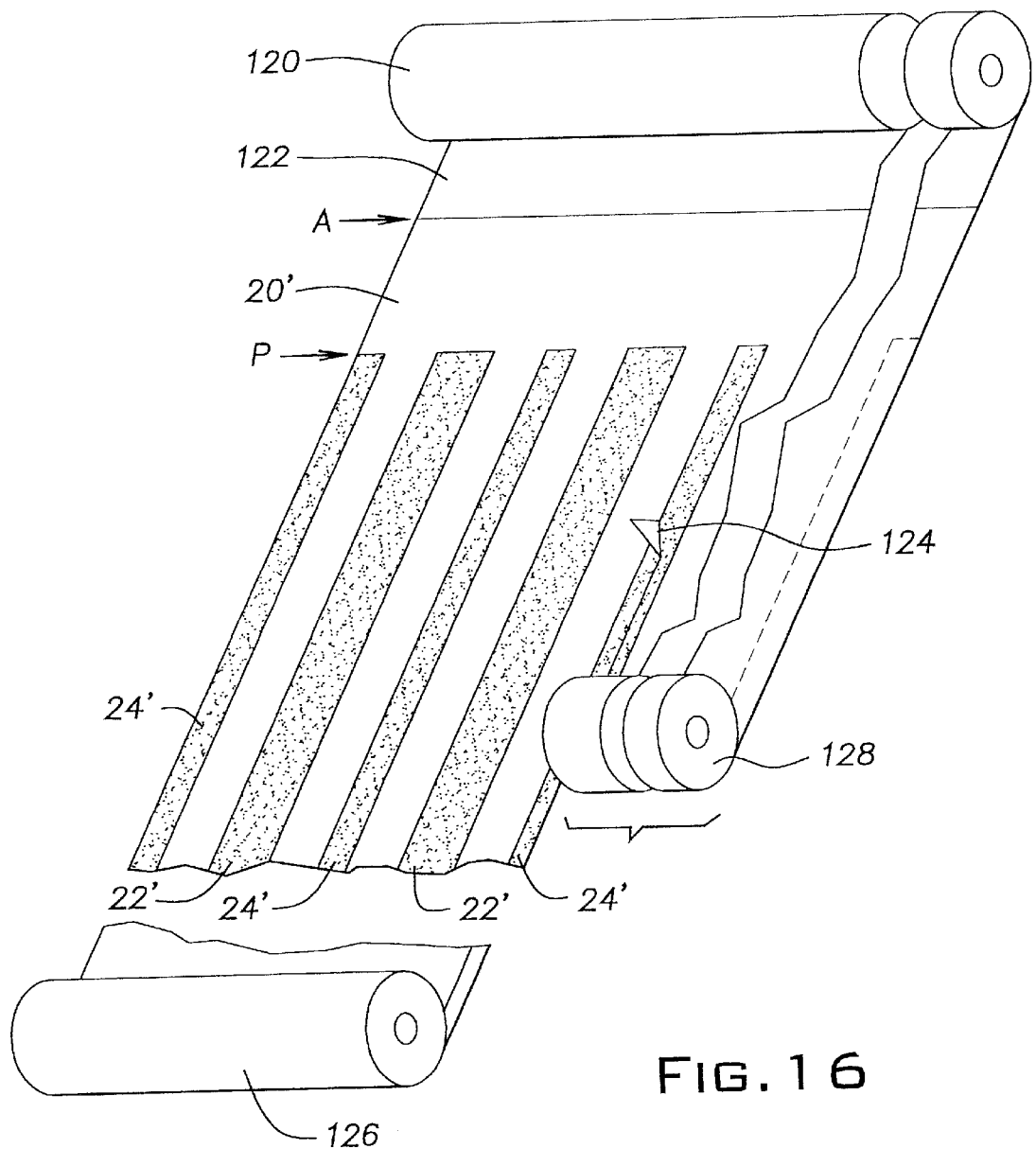
FIG. 16 is a schematic isometric view illustrating coating and slitting practices in preparation of transfer tape stock in accordance with another aspect of the invention.

Referring to FIG. 16, the manufacture of a transfer tape in accordance with the present invention is illustrated. In the manufacture of transfer tape, a roll 120 is provided comprising a web of release liner substrate 122 which is coated on both sides with release coatings (not shown) either in prior coating operations before forming of the roll 120 or as initial coating and drying steps (not shown) following off-feed from roll 120. A suitable choice for liner in the practice of the invention is 80# "super Tough" which is commercially available from Otis Paper.

At the adhesive-applying station A, a layer of adhesive 20' is applied to the substrate 122 continually across the width of the substrate 122. The adhesive-coating step may be performed in the absence of any patterning, as shown, or less preferably there may be patterning at the side edges.

Following application of the adhesive layer 20', adhesive-inhibiting masking layers 22' and 24' are applied at a printing station P. The masking may be an ink applied with a flexographic printing press or laser printer (not shown), whose positions across the width of the adhesive coating 20' may be readily adjusted as desired to thereby determine tape width. Preferably, the masking is applied at the side edges, as shown in dotted outline, as well as at intermediate portions of the web.

Following drying of the masking, employing drying means if required (not shown), the adhesive-coated stock is then slit by a slitter 124. Slitting may also be performed at the side edges if edge trimming is required, but slitting at only the central location a shown to simplify the illustration. The slit stock is then self-wound to form the individual transfer tape roll 126, and reserve roll 128 of adhesive-coated stock.

The adhesive face of the transfer tape roll 126 can be applied to tape facestock 18' to form tape stock 10' as shown in FIG. 13. Alternatively, the extensible layer 26' may be applied to the masking layer 22' to form the tape stock 10' as shown in FIG. 14. In either case, the release liner substrate 122 will protect the adhesive layer 20' until it is further processed to form a fastening tape or diaper tab. Accordingly, the transfer tape roll 126 may be self-wound with the release coat on the other face of substrate 122 having a harder release to enable subsequent release and transfer of the adhesive layer, masking layer and extensible layer assembly to the facestock 18'. Optionally, a known conveying mechanism such as a release belt (not shown) may be arranged to provide temporary support of the separated adhesive layer, masking layer and extensible layer assembly as it is transferred to the facestock 18'. Of course, a second substrate may be used with the layers sandwiched therebetween to form a multi-substrate transfer tape stock.

The stock in the reserve roll 128 is not "committed" to specific roll widths. Thus, the adhesive-coated reserve roll 128 may be passed through the printing station P to receive the adhesive-inhibiting masking 22 and 24 as required to produce additional transfer tape stock.

Converters of tapes and other products using the printed adhesive masking of the present invention can handle the adhesive tapes or stocks efficiently. The rolls can be tightly wound. There is little or no cutting differential between masked and unmasked adhesive areas. The rolls unwind in a uniform manner. The risk of edge damage (nicking) of the rolls is reduced.

As described above, in the foregoing examples of the invention, the printing of the adhesive barrier is along a continuous zone or line, and the tape is formed in whole or in part by slitting along that continuous line through the tape substrate, an adhesive coating, and the printed barrier.

The invention is not limited to the specific details of the disclosed embodiments, but is defined in the following claims.

What is claimed is:

1. A method of manufacturing stretchable tape stock comprising the steps of feeding a nonextensible layer along a manufacturing line, combining a layer of pressure-sensitive adhesive with said nonextensible layer, applying a patterned adhesive-inhibiting masking to define a masking pattern comprising at least one continuous line extending along a face of said adhesive, and applying an extensible layer over at least a part of said continuous masking line to inhibit adhesion and enable relative movement between said extensible layer and adhesive layer.

2. A method as set forth in claim 1, wherein said step of applying said patterned adhesive-inhibiting masking and the step of applying said extensible each include one of printing, lamination, extrusion, and coextrusion.

3. A method as set forth in claim 2, wherein said adhesive-inhibiting masking extends along a face of said adhesive layer remote of said nonextensible layer.

4. A method as set forth in claim 1, further including forming a separation line extending in the machine direction in said nonextensible layer, said separation line being formed during preparation of said tape stock or thereafter.

5. A method as set forth in claim 4, wherein said separation line is formed by mechanical or chemical processing of said nonextensible layer.

6. A method as set forth in claim 4, wherein said step of forming said separation line comprises one of forming a full cleavage or parting of adjacent portions of said nonextensible layer and forming a location of weakened separation strength in said nonextensible layer.

7. A method as set forth in claim 1, wherein said nonextensible layer is a tape facestock and further including the step of combining said tape stock with a release tape stock to form a diaper tab stock.

8. A method as set forth in claim 1, wherein said tape stock is sized to form a plurality of tapes extending in the transverse machine direction across said tape stock, each of said tapes including a central segment having a terminal segment on each side thereof, and further including forming said masking pattern with a plurality of said continuous masking lines, one of said continuous masking lines extending through each of said central segments of said tapes, and applying a plurality of said extensible layers to said tape stock, one of said extensible layers extending over at least a part of an associated one of said continuous masking lines.

9. A method as set forth in claim 8, wherein said nonextensible layer is a tape facestock formed of a film forming thermoplastic and said extensible layers are formed of a thermoplastic elastomer, and the steps of applying said continuous masking lines and said extensible layers over associated continuous masking lines each include one of printing, lamination, extrusion, and coextrusion.

10. A method as set forth in claim 9, further including forming a separation line extending in the machine direction in said tape facestock along each of said central segments, said separation lines being formed during preparation of said tape stock or thereafter.

11. A method of manufacturing transfer tape stock for use in making stretchable tape comprising the steps of feeding a first substrate along a manufacturing line, combining a layer of pressure-sensitive adhesive with a first face of said substrate, applying to said layer of pressure-sensitive adhesive a patterned adhesive-inhibiting masking to define a masking pattern comprising at least one continuous line, combing said at least one continuous line of masking with an extensible layer, and further processing said transfer tape stock by releasably combining the side of said pressure-sensitive adhesive layer bearing said masking and extensible layer against a second substrate face, said second substrate face comprising the other face of said first-named substrate to thereby produce a self-wound transfer tape stock or comprising the face of an additional substrate to thereby produce a multi-substrate transfer tape stock.

12. A method as set forth in claim 11, wherein said masking pattern includes a second continuous line and further including the step slitting said substrate, adhesive layer and masking along said at second continuous line defined by said pattern coating to form a slit transfer tape stock.

13. A method as set forth in claim 11, wherein said step of applying said masking pattern and the step of combining said extensible layer each include one of printing, lamination, extrusion and coextrusion.

14. A method as set forth in claim 11, further including forming a separation line extending in the machine direction in said extensible layer, said separation line being formed during preparation of said transfer tape stock or thereafter.

15. A method as set forth in claim 14, further including the step of transferring said adhesive layer, masking layer and extensible layer from said substrate to a facestock to form a stretchable tape stock.

* * * * *